United States Patent [19]

Eiter

[11] 3,940,425

[45] Feb. 24, 1976

[54] PROCESS FOR THE PRODUCTION OF POLYUNSATURATED COMPOUNDS

[75] Inventor: Karl Eiter, Cologne, Germany

[73] Assignee: Bayer Aktiengesellschaft, Germany

[22] Filed: Aug. 28, 1974

[21] Appl. No.: 501,227

[30] Foreign Application Priority Data

Sept. 6, 1973 Germany............................ 2344985
May 28, 1974 Germany............................ 2425813

[52] U.S. Cl.... 260/345.9; 260/448.2 E; 260/485 R; 260/486 R; 260/533 N; 260/561 N; 260/615 A; 260/632 Y; 260/635 Y; 260/678

[51] Int. Cl.[2].................. C07D 309/22; C07F 7/02

[58] Field of Search............ 260/678, 635 Y, 632 Y, 260/561 N, 486 R, 485 R, 448.2 E, 345.9, 615 A, 617 E, 533 N

[56] References Cited

UNITED STATES PATENTS

| | | | |
|---|---|---|---|
| 2,222,394 | 11/1940 | Berg et al. ......................... | 260/678 |
| 2,846,491 | 8/1958 | Rutledge............................. | 260/678 |
| 2,884,464 | 4/1959 | Kurtz................................... | 260/678 |

OTHER PUBLICATIONS

Rutledge, "Acetylenic Compounds," pp. 84–96, (1968).
Sevin et al., Tetrahedron Letters, pp. 1953–1959, (1965).
Stephens et al., J. Org. Chem., 28, 3313 (1963).
Bourgain et al., Chem. Abstract, 71, 80580t (1969).

*Primary Examiner*—James O. Thomas, Jr.
*Assistant Examiner*—Nicky Chan

[57] ABSTRACT

Compounds of the formula $$R^1-C \equiv C-R^2 \qquad (I)$$

wherein $R^1$ is hydrogen, unsubstituted or substituted alkyl, unsubstituted or substituted alkenyl, unsubstituted or substituted alkynyl, unsubstituted or substituted polyalkenyl, or unsubstituted or substituted polyalkynyl, and $R^2$ is unsubstituted or substituted alkenyl, unsubstituted or substituted alkynyl, unsubstituted polyalkenyl or unsubstituted or substituted polyalkynyl, are produced by reacting a compound of the formula $$R^1-C \equiv CH \qquad (II)$$

wherein $R^1$ is as above defined in a mixture comprising a copper(I) halide or copper(I) cyanide, a bicyclic amidine base and a catalytic amount of an antioxidant or mixture of antioxidants, in an organic solvent or mixture of solvents, at a temperature of from −40° C to +100° C, with a compound of the formula $$X-R^2 \qquad (III)$$

wherein

X is halogen, and
$R^2$ is as above defined.

20 Claims, No Drawings

PROCESS FOR THE PRODUCTION OF POLYUNSATURATED COMPOUNDS

The present invention relates to a process for the production of compounds with polyunsaturation, that is, compounds having multiple points of unsaturation. The compounds produced according to the present process are generally known and said known compounds, together with any novel compounds which may be obtained according to the process of the present invention, are useful as intermediates for the synthesis of insect-attracting substances. A process for the conversion of a representative compound of the present invention into "Dispalur", which is a known insect-attracting substance, is set forth below.

It is known that polyacetylene compounds with triple bonds isolated from one another can be synthesized as follows:

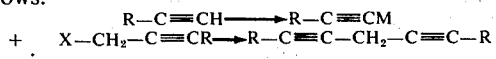

$$R-C\equiv CH \longrightarrow R-C\equiv CM$$
$$+ X-CH_2-C\equiv CR \longrightarrow R-C\equiv C-CH_2-C\equiv C-R$$

wherein
R is hydrogen or any desired organic moiety,
M is Li, Na, K or —MgX, and
X is halogen.

According to this earlier disclosure, the monoacetylene compound is converted into the acetylene-metal compound, which in turn is reacted, using a great variety of solvents, with a halide of a second acetylene compound, whereupon alkylation of the acetylenic carbon atoms occurs (see L. Brandsma, *Preparative Acetylenic Chemistry*, Elshevier Publishing Co., Amsterdam, 1971).

In this prior art process it is necessary to react an acetylene starting compound with a lithium alkyl, alkali metal, alkali metal hydride, Grignard compound or the like, in order to metallize the acetylenic methine proton and subsequently to effect reaction with a propargyl halide, an $\alpha,\beta$-unsaturated halide or a derivative thereof, or with an ordinary alkyl halide. The metallizing agents, which present a fire hazard and can only be used in inflammable solvents, thus hardly permit industrial use of such reagents.

Moreover, in the process steps mentioned above, for the synthesis of highly unsaturated compounds, either under the reaction conditions which prevail, or as a result of the action of the reactants on the synthesized, isolated polyacetylene compounds, undesired isomerizations, ranging from allene formation to propargyl rearrangement can occur extensively, and the isomer mixtures obtained, which contain impurities to a greater or lesser extent, exhibit a tendency to decompose explosively.

The present invention provides a process for the preparation of unsaturated compounds of the formula $$R^1-C\equiv C-R^2 \qquad (I)$$

wherein
R$^1$ is hydrogen, unsubstituted or substituted alkyl, especially alkyl of 1 to 12 carbon atoms, unsubstituted or substituted by tetrahydropyranyloxy, tri-lower alkylsilyl, hydroxy, carboxyl, carbo-lower alkoxy, carboxylic acid amide or a moiety of the formula

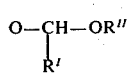

wherein
R$^I$ and R$^{II}$ are alkyl of 1 to 5 carbon atoms; unsubstituted or substituted alkenyl, especially alkenyl of 2 to 12 carbon atoms, unsubstituted or substituted by tetrahydropyranyloxy, tri-lower alkylsilyl, hydroxy, carboxyl, carbo-lower alkoxy, carboxylic acid amide or a moiety of the formula

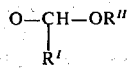

wherein
R$^I$ and R$^{II}$ are alkyl of 1 to 5 carbon atoms, unsubstituted or substituted alkynyl; especially alkynyl of 2 to 12 carbon atoms, unsubstituted or substituted by tetrahydropyranyloxy, tri-lower alkylsilyl, hydroxy, carboxyl, carbo-lower alkoxy, carboxylic acid amide or a moiety of the formula

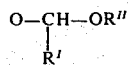

wherein
R$^I$ and R$^{II}$ are alkyl of 1 to 5 carbon atoms, unsubstituted or substituted polyalkenyl, i.e., alkenyl having multiple points of unsaturation; especially polyalkenyl of 2 to 12 carbon atoms, unsubstituted or substituted by tetrahydropyranyloxy, tri-lower alkylsilyl, hydroxy, carboxyl, carbo-lower alkoxy, carboxylic acid amide or a moiety of the formula

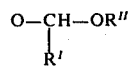

wherein
R$^I$ and R$^{II}$ are alkyl of 1 to 5 carbon atoms; or unsubstituted or substituted polyalkynyl, i.e., alkynyl having multiple points of unsaturation, especially polyalkynyl of 2 to 12 carbon atoms, unsubstituted or substituted by tetrahydropyranyloxy, tri-lower alkylsilyl, hydroxy, carboxyl, carb-lower alkoxy, carboxylic acid amide or a moiety of the formula

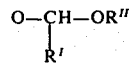

wherein
R$^I$ and R$^{II}$ are alkyl of 1 to 5 carbon atoms; and
R$^2$ is unsubstituted or substituted alkenyl, especially alkenyl of 2 to 12 carbon atoms, unsubstituted or substituted by tetrahydropyranyloxy, tri-lower alkylsilyl, hydroxy, carboxyl, carb-lower alkoxy, carboxylic acid amide or a moiety of the formula

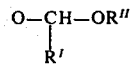

wherein
R$^I$ and R$^{II}$ are alkyl of 1 to 5 carbon atoms; unsubstituted or substituted alkynyl, especially alkynyl of 2 to 12 carbon atoms, unsubstituted or substituted by tetrahydropyranyloxy, tri-lower alkylsilyl, hydroxy, carboxyl, carb-lower alkoxy, carboxylic acid amide or a moiety of the formula

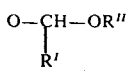

wherein
R' and R'' are alkyl of 1 to 5 carbon atoms; unsubstituted or substituted polyalkenyl, i.e., alkenyl having multiple points of unsaturation, especially polyalkenyl of 2 to 12 carbon atoms, unsubstituted or substituted by tetrahydropyranyloxy, tri-lower alkylsilyl, hydroxy, carboxyl, carb-lower alkoxy, carboxylic acid amide or a moiety of the formula

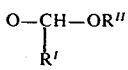

wherein
R' and R'' are alkyl of 1 to 5 carbon atoms; or unsubstituted or substituted polyalkynyl, i.e., alkynyl having multiple points of saturation, especially polyalkynyl of 2 to 12 carbon atoms, unsubstituted or substituted by tetrahydropyranyloxy, tri-lower alkylsilyl, hydroxy, carboxyl, carb-lower alkoxy, carboxylic acid amide or a moiety of the formula

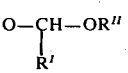

wherein
R' and R'' are alkyl of 1 to 5 carbon atoms, which process comprises reacting a compound of the formula $R^1$—CH   CH    (II)

wherein
$R^1$ is as above defined,
in a reaction mixture which comprises a copper(I) halide or copper(I) cyanide, a bicyclic amidine base and a catalytic amount of an antioxidant or mixture of antioxidants, either in the presence or in the absence of water, in an organic solvent or mixture of such solvents, at a temperature of from −40° C to +100° C, with a compound of the formula

X—$R^2$    (III)

wherein
X is halogen, and
$R^2$ is as above defined.

It is distinctly surprising that according to the above reaction sterically pure compounds with multiple points of unsaturation can be synthesized in a high yield without rearrangement occurring whereby major amounts of isomeric end products would result.

The following may be mentioned as examples of starting compounds of the formula (II): 3-tetrahydropyranyloxypropyne-(1), heptyne-(1), pentyne-(1), propargyl alcohol, propyn-(1)-ol(3), butyn-(1)-ol(4), pentyn-(1)-ol(5), undecadiyn-(2,5)-ol(1), decadiyn(2,5)-ol-(1), nonadiyn-(2,5)-ol-(1), heptadiyn-(2,5)-ol-(1), octadiyn-(2,5)-ol-(1), hexadiyn-(2,5)-ol-(1), nonadiyn-(1,4)-ol-(9), propyne-(1), butyne-(1), hexyne-(1), octyne-(1), nonyne-(1) and decyne-(1).

The following may be mentioned as examples of starting compounds of the formula (III): 3-trimethylsilyl-propargyl bromide, 3-trimethylsilyl-propargyl chloride, 3-trimethyl-silylpropargyl iodide, allyl chloride, allyl bromide, allyl iodide, 1-chloro-4-tetrahydropyranyloxybutyne-(2), 1-bromo-4-tetrahydropyranyloxybutyne-(2), 1-iodo-4-tetrahydropyranyloxybutyne-(2), 1-chlorooctyne-(2), 1-bromooctyne-(2), 1-iodo-octyne-(2), 1-chloroundecadiyne-(2,5), 1-bromoundecadiyne-(2,5), 1-iodoundecadiyne-(2,5), 1-iodobutyne-(2), 1-iodo-pentyne-(2), 1-iodoheptadiyne-(2,5), 1-iododecatriyne-(2,5,8), 1-iodotridecatetrayne-(2,5,8,11) and 1-iodooctadiyne-(2,5).

Some of the compounds of the formulas (II) and (III) employed as starting compounds are known. However, they can all be prepared easily in accordance with known methods.

Thus, for example, halides of the formula (III), especially iodides, are prepared by reaction of tosylates or mesylates of the corresponding alcohols with alkali metal halides, preferably NaI, in polar solvents, preferably in acetone.

If 3-tetrahydropyranyloxypropyne-(1) and allyl bromide are used as starting compounds, the course of the reaction can be represented by the following equation:

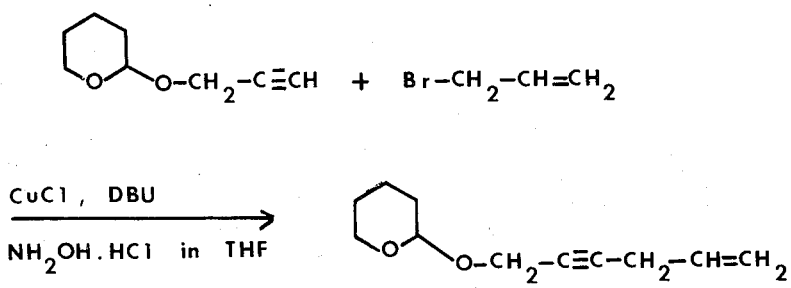

DBU = 1,8-diazabicyclo[5,4,0]undecene
THF = tetrahydrofuran.

The tetrahydropyranyloxy derivative can be converted, by subsequent acid hydrolysis, into the corresponding hydroxy compound:

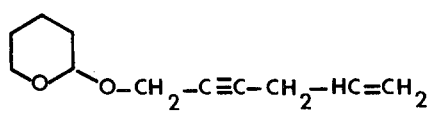

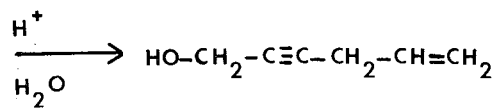

If propargyl alcohol and allyl bromide are used as starting compounds and the reaction is carried out in the presence of CuI or CuBr, using diazabicycloundec-ene (DBU) in an organic solvent consisting of absolute tetrahydrofuran (THF) and/or hexamethylphosphoric acid triamide (HEMPTA), the reaction can be represented by the following equation:

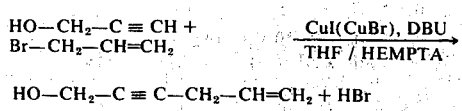

$$HO-CH_2-C \equiv C-CH_2-CH=CH_2 + HBr$$

In formula (II), $R^1$ is preferably alkyl, alkenyl or alkynyl as hereinabove defined.

In formula (III), $R^2$ is preferably alkenyl, polyalkenyl, alkynyl or polyalkynyl as hereinabove defined.

Preferred compounds of the formula (III) are compounds of the formulas

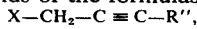

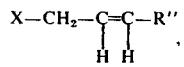

and

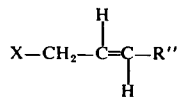

wherein

X is preferably bromine or iodine and

R″ is preferably hydrogen, trialkylsilyl, especially tri-lower alkylsilyl and most especially trimethylsilyl, tetrahydropyranyloxy, carboxyl, carbalkoxy, especially carb-lower alkoxy, or a carboxylic acid amide whicch may be substituted on the amide nitrogen.

According to one embodiment of the present invention.

$R^1$ is alkyl of 1 to 12 carbon atoms, alkenyl of 2 to 12 carbon atoms, alkynyl of 2 to 12 carbon atoms, or said alkyl, said alkenyl or said alkynyl substituted by tetrahydropyranyloxy, tri-alkylsilyl of 1 or 2 carbon atoms, or hydroxy, and $R^2$ is alkenyl of 2 to 12 carbon atoms, alkynyl of 2 to 12 carbon atoms, or said alkenyl or alkynyl substituted by tetrahydropyranyloxy, tri-alkylsilyl of 1 or 2 carbon atoms or hydroxy.

According to another embodiment of the present invention compound X—R² is

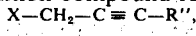

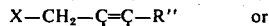 or

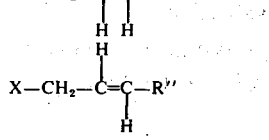

X is bromine or iodine and

R″ is hydrogen, trialkylsilyl of 1 to 2 carbon atoms, carboxyl, carbalkoxy or carboxylic acid amide.

According to another embodiment of the present invention

R″ is hydrogen, allyl or tri-methylsilyl.

All inert organic solvents can be used as diluents in the reaction according to the invention, especially acetonitrile, tetrahydrofuran (THF), dimethylformamide (DMF), benzene, dioxane, dimethylsulphoxide (DMSO), hexamethylphosphoric acid triamide (HEMPTA) and mixtures of the aforesaid solvents.

Equally, the reaction can also be carried out in the presence of some water together with the organic solvent.

The reaction according to the invention is carried out in the presence of a bicyclic amidine, preferably 1,5-diazabicyclo[4,3,0]nonene (DBN) or 1,8-diazabicyclo[5,4,0]undecene (DBU), and of copper(I) salts, preferably CuCl, CuBr, CuI and CuCN, with a catalytic amount of an antioxidant or a mixture of antioxidants.

Representative antioxidants which may be used in the process of the present invention include: hydroxylammonium salts, for example the hydrochloride or the sulphate, phenothiazine, hydrazine, hydrazinium salts, such as hydroazinium chloride, ascorbic acid and tertiary butylphenols, for example, 2,6-bis-tert.-butylphenol, or mixtures thereof.

A preferred temperature range for the process according to the present invention is from −10° C to +60° C.

In general the reaction is carried out at atmospheric pressure and in an inert gas atmosphere.

To carry out the process according to the present invention, the equimolar amount of Cu(I) salt is first introduced into the solvent under a nitrogen atmosphere and catalytic amounts of the antioxidant are added while cooling, as are 1 to 1.5 equivalents of the cyclic amidine base, added dropwise until solution has occurred. While continuing always to work under an inert gas atmosphere, 1 to 1.5 equivalents of the acetylene compound are now added with stirring. The desired halide, dissolved in the same solvent or different solvents, is now added slowly, and the mixture must be cooled if the reaction temperature rises suddenly.

The reaction batch is worked up by introducing it into ice/ammonium chloride. Remanants of copper salt which are found are filtered off if necessary. The mixture is then extracted with a readily volatile organic solvent and the organic phase is washed with ammonium chloride solution and water. The organic phase is then dried and the solvent is evaporated. The highly unsaturated compound can be obtained in yields of between 50 and 100 percent of theory.

The compounds according to the present invention are valuable intermediates for the preparation of active final products such as, for example, for the synthesis of the insect-attracting substances "Dispalur" (7,8-cis-epoxy-2-methyl-octadecane, the insect-attracting substance of the gypsy moth (*Porthetria dispar*)) and "Muscalur" (9-cis-tricosene) (see, on this subject, K. Eiter, Naturwissenschaften 10, 468–69 (1972) and K. Eiter, Angew. Chem. 84, 67–68 (1972)).

By way of example, the following reaction path is proposed for the preparation of Dispalur:

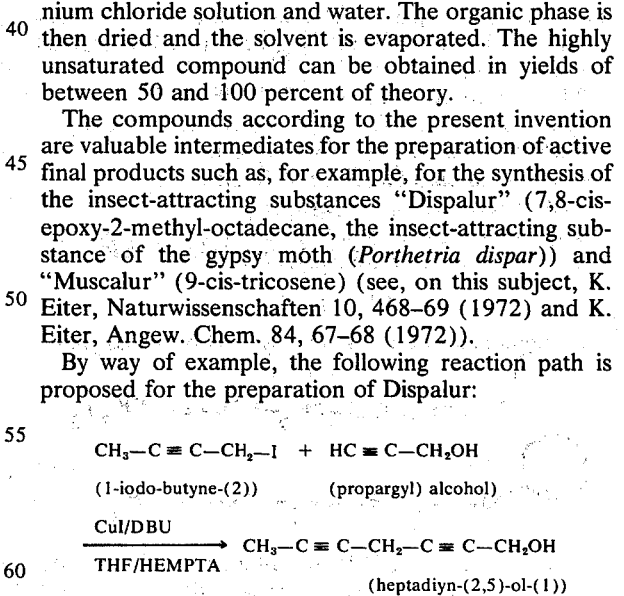

Heptadiyn-(2,5)-ol-(1) is converted into the corresponding 1-iodoheptadiyne-(2,5) via the tosylate, by reaction with NaI, and this is further reacted as follows:

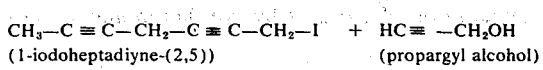

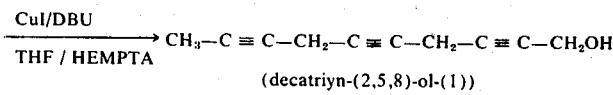
(decatriyn-(2,5,8)-ol-(1))

The resulting decatriyn-(2,5,8)-ol-(1) is in turn converted into the corresponding iodide via the tosylate, with NaI, in a known manner.

Finally, the 1-iodo-decatriyne-(2,5,8) thus produced is perhydrogenated to 1-iododecane:

$$CH_3-C\equiv C-CH_2-C\equiv C-CH_2-C\equiv C-CH_2I$$
$$+ 6H_2 \rightarrow CH_3-(CH_2)_9-I$$

The 1-iododecane is further converted into "Dispalur" as follows:

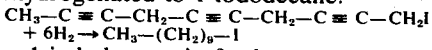
(dodecyne-(1))

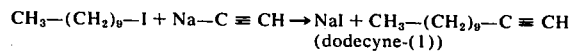

(M = —Na, —Li, —MgX)

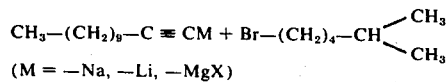

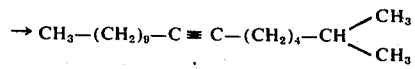
(2-methyl-octadecene-(7-cis))

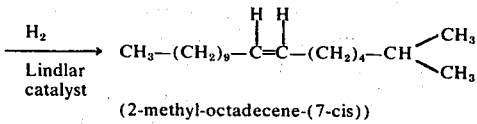

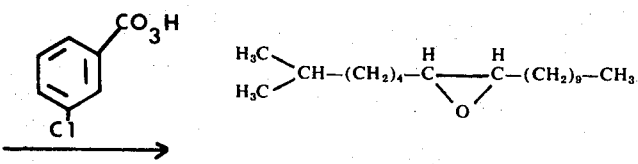

(7,8-cis-epoxy-2-methyl-octadecane, "Dispalur")

The process of this invention is illustrated in the preparative examples which follow, wherein the following abbreviations, the meaning of which is explained here, are used:

THF = tetrahydrofuran
HEMPTA = hexamethylphosphoric acid triamide
DBN = 1,5-diazabicyclo[4.3.0]nonene
DBU = 1,8-diazabicyclo[5.4.0]undecene
THP = tetrahydropyranyloxy The following nonlimitative examples more particularly illustrate the present invention:

EXAMPLE 1

1-Trimethylsilyl-6-tetrahydropyranyloxyhexadiyne-(1,4)

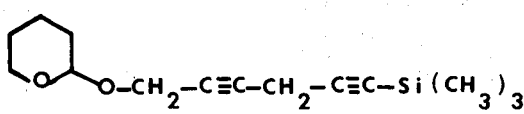

(1)

100 ml of absolute THF and 14.8 g (0.15 M) of anhydrous CuCl were initially introduced, in a nitrogen atmosphere, into a stirring apparatus, while cooling at 0°C. 18.6 g (0.15 M) of DBN were then added dropwise and the dark green complex solution was decolorized by addition of 2.0 g of hydroxylammonium chloride; 21.0 g (0.15 M) of 3-tetrahydropyranyloxypropyne-(1) in 10 ml of absolute THF were then added dropwise while continuously passing very pure nitrogen through the mixture, and a solution of 19.1 g (0.1 M) of silylated propargyl bromide dissolved in 20 ml of absolute THF was allowed to run in at 0°C. After stirring for 8–12 hours, the mixture was poured onto ice and ammonium chloride, remnants of copper salt were filtered off and the aqueous filtrate was repeatedly extracted with ether. After washing with water, the organic phase was dried and the solvent was carefully removed in a rotary vacuum evaporator. Yield: 25.0 g of a product which, according to the IR and NMR spectra, contained traces of the initial tetrahydropyranyloxypropyne in addition to traces of allene. The product could be treated, for further conversion, by subjecting it to chromatography on silica gel, from which it was easily eluted as the peak fraction with the eluant petroleum ether:ether (9:1). IR: 2,195 cm$^{-1}$, 2,250 cm$^{-1}$, 1,250 cm$^{-1}$, 1,120 cm$^{-1}$ and 1,020–1,080 cm$^{-1}$. These spectrographic data unambiguously indicate 1-trimethylsilyl-6-tetrahydropyranyloxyhexadiyne-(1,4).

EXAMPLE 2

6-Tetrahydropyranyloxy-hexen-(1)-yne-(4)

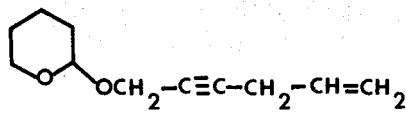

A complex solution was prepared from 9.9 g (0.1 M) of CuCl and 18.6 g (0.15 M) of DBU in 100 ml of absolute THF under nitrogen; after addition of 1.0 g of hydroxylamine hydrochloride, the solution became completely colorless. After cooling to 0°–10°C, 21.0 g (0.15 M) of 3-tetrahydropyranyloxypropyne-(1) were rapidly added dropwise, followed by 24.0 g (0.2 M) of allyl bromide. The reaction was strongly exothermic (the temperature rose to +60°C). The mixture was then heated for a further 30 minutes at 60°C and worked up as described in Example 1. 25.0 g of a yellowishtinged oil, which distilled in a high vacuum (boiling point = 73°–75°C/0.1 mm Hg) without leaving a residue, were obtained. According to the IR spectrum and NMR spectrum, the oil was the pure product referred to above. $n_D^{20} = 1,4774$. IR: 3,040; 2,900; 2,850; 2,220; 2,280; 1,640; 1,440; 1,420; 1,390; 1,340; 1,325; 1,285; 1,265; 1,200; 1,185; 1,120 1,020–1,080; 985; 945; 900; 868 and 820 cm$^{-1}$.

EXAMPLE 3

1-Tetrahydropyranyloxyundecadiyne-(2,5)

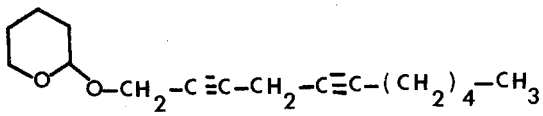

A solution of a complex was prepared from 100 ml of absolute THF and 14.8 g (0.15 M) of CuCl, 18.6 g (0.15 M) of DBN and 2.0 g of hydroxylamine hydrochloride at 0°C, taking care to flush the mixture well with nitrogen. 14.4 g (0.15 M) of heptyne-(1) were introduced into this complex at 0°C and thereafter 23.3 g (0.1 M) of 1-bromo-4-tetrahydropyranyloxybutyne-(2) in 20 ml of absolute HEMPTA were allowed to run in. The temperature was raised to +60°C and the mixture was stirred for 6 hours at this temperature. Working up gave 23.0 g of an oil which was freed from excess 3-tetrahydropyranyloxypropyne-(1) in a high vacuum; the residue was a halogen-free product, the IR and NMR spectra of which showed that the compound was in the form of the isolated diyne of the desired structure.

IR: 2,900, 2,220; 2,260 (doublet); 1,440–1,470 (triplet); 1,385; 1,345; 1,320; 1,265; 1,210; 1,180; 1,120; 1,080; 1,060; 1,020; 975; 950; 910; 875 and 820 cm$^{-1}$.

NMR: 4.85 ppm (M)

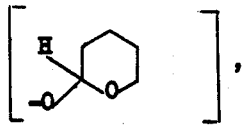

4.20 ppm (T), 3.15 ppm (M)— [—C ≡ C—CH$_2$—C ≡ C], (I = 7 Hz), 3.35–3.8 ppm (M)

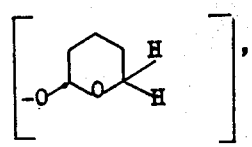

0.95–2.2 ppm [remaining protons]

EXAMPLE 4

1,7-Bis-tetrahydropyranyloxy-heptadiyne-(2,5)

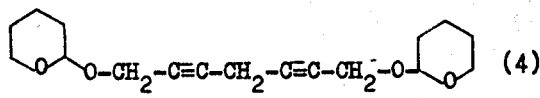 (4)

A complex was prepared from 100 ml of absolute THF, 14.8 g (0.15 M) of CuCl and 18.6 g (0.15 M) of DBN under a N$_2$ atmosphere, and was immediately obtained colorless as a result of the addition of 2.0 g of NH$_2$OH.HCl. 21.0 g (0.15 M) of tetrahydropyranyloxy-propyne-(1) in 20 ml of absolute THF were added at 0°C, followed by a solution of 23.3 g (0.1 M) of 1-bromo-4-tetrahydropyranyloxy-butyne-(2) in 20 ml of absolute HEMPTA, added dropwise. The mixture was warmed to 60°C for 6 hours while flushing with N$_2$ and was then worked up in the usual manner. Yield: 23.5 g of an orange oil which contained a little excess tetrahydropyranyloxy-propyne, but which could be purified, by removing the latter, either by separation in a high vacuum until the temperature at which material passed over reached 50°C, or by chromatography on a silica gel column, using petroleum ether; ether (9:1). The IR spectrum and NMR spectrum proved the structure.

IR: 2,210 (shoulder); 2,270 cm$^{-1}$ (weak); 1,945 cm$^{-1}$ (medium-strong); and broad and very strong bands at 1,120 and 1,000–1,080 cm$^{-1}$.

NMR: 3.25 ppm (T), 4.8 ppm (M), 4.25 ppm (M), 3.5–3.9 ppm (M), 1.68 ppm, remaining protons; 5.5 ppm (olefinic protons of the allene isomer, in traces).

EXAMPLE 5

1-Tetrahydropyranyloxyundecadiyne-(2,5)

A solution of a complex was prepared from 50 ml of absolute benzene, 15.2 g (0.1 mole) of DBU and 14.3 g (0.1 mole) of CuBr under an argon atmosphere. After adding catalytic amounts of phenothiazine and ascorbic acid, the mixture was warmed to 40°C and a solution of 10.0 g (0.1 mole) of heptyne-(1) in 30 ml of absolute benzene was added. This produced a yellow-green suspension which was stirred for 30 minutes at 30°–40°C. 23.3 g (0.1 mole) of 1-bromo-4-tetrahydropyranyloxy-butyne-(2) in 50 ml of absolute benzene were then allowed to run in and the mixture was warmed to 40°–50°C. The whole was stirred for 4 hours at 40°–50°C, which produced a dark orange solution in addition to a solid which could be stirred easily. Decomposition was effected analogously to Example 1 with ice/NH$_4$Cl. The mixture was repeatedly extracted with ether and the extract was dried and clarified with active charcoal, thus giving 25.0 g (100% of theory) of a light yellow oil which after filtration through Al$_2$O$_3$ of activity II (acid), using petroleum ether/ether (7/3), gave 24.0 g of what, according to the IR spectrum and NMR spectrum, was the product referred to above. The NMR spectrum was completely identical to that found in Example 3.

EXAMPLE 6

1-Tetrahydropyranyloxy-undecadiyne-(2,5)

28.5 g (0.15 mole) of CuI (very finely powdered and dried) were added to 50 ml of absolute benzene and 23.0 g (0.15 mole) of DBU in an argon atmosphere, and after lightening the color of the complex by adding 0.1 g of hydroxylammonium sulphate and a pinch of phenothiazine, a solution of 15.0 g (0.15 mole) of heptyne-(1) was introduced. The mixture was stirred for one-half hour at 40°C and at this temperature a solution of 28.1 g (0.1 mole) of 4-tetrahydropyranyloxyiodobutyne-(2) in 50 ml of absolute benzene was rapidly added dropwise. The temperature rose gradually to 50°C, the mixture was stirred for 2 hours at this temperature, the residue which had separated out was filtered off after cooling the contents of the flask and was washed with ether and the filtrate was repeatedly extracted by shaking with ice water/$NH_4Cl$, rinsed with a little dilute $Na_2S_2O_3$ solution and $H_2O$, dried and evaporated in vacuo. Residue 24.0 g (96% of theory). The IR and NMR spectra were identical to those of the product of Example 3.

Undecadiyn-(2,5)-ol-(1)

38.0 g (0.25 mole) of DBU were dissolved in 150 ml of absolute THF and 30 ml of absolute HEMPTA under argon, and 47.5 g (0.25 mole) of very finely powdered CuI were added thereto, in portions. After adding catalytic amounts of hydroxylammonium sulphate (0.3 g) and phenothiazine (0.2 g), a solution of 20.0 g (0.25 mole) of freshly distilled propargyl alcohol (propyn-(1)-ol-(3)) in 10 ml of absolute HEMPTA was added dropwise. After stirring at 50°C in an argon atmosphere, the yellow paste produced became somewhat more fluid after 30 minutes. A solution of 42.0 g of 1-iodooctyne-(2) (0.18 mole) in 50 ml of absolute HEMPTA was then added dropwise and the mixture was stirred at 50°C for 6 hours. After evaporating off the bulk of the THF in a rotary evaporator, the pasty residue was decomposed with $NH_4Cl$/ice water and the mixture extracted with ether in an extractor. After washing with water, drying and evaporation, the ether extract gave 35.0 g of an oil which was a mixture of undecadiyn-(2,5)-ol-(1) with a little HEMPTA.

EXAMPLE 8

Hexen-(5)-yn-(2)-ol-(1)

A solution was prepared from 100 ml of absolute THF and 15.7 g (0.1 mole) of DBU in a nitrogen atmosphere, and 19.0 g (0.1 mole) of CuI were added thereto at room temperature. The mixture was stirred until the CuI had dissolved completely. A pinch of hydroxylammonium sulphate and phenothiazine were added, followed by 30 ml of absolute HEMPTA, a solution of 6.0 g (0.11 mole) of propargyl alcohol in 30 ml of absolute THF was added dropwise at 40°C, the yellow paste was stirred for 1 hour at room temperature, and 16.0 g of allyl bromide (0.13 mole) were then added dropwise. The temperature rose to 50°–60°C and the mixture was stirred for 2 hours at 60°C, during which the contents of the flask dissolved completely. After decomposition with ice/$NH_4Cl$, the mixture was exhaustively extracted with ether in an extractor, the ether was distilled off under normal pressure and the residue was distilled in vacuo: the boiling point was 76°–80°C/12 mm Hg. Yield: 8.0 g of a colorless liquid (84% of theory); $n_D^{20}$ 1.4760. The IR spectrum and NMR spectrum agreed in all details with the structure.

EXAMPLE 9

Tetradecatriyn-(2,5,8)-ol-(1)

A solution of a complex was prepared from 100 ml of absolute THF, 20 ml of absolute HEMPTA, 7.6 g (0.05 mole) of DBU and 9.5 g (0.05 mole) of CuI in a nitrogen atmosphere, and after adding catalytic amounts of phenothiazine and hydroxylammonium sulphate, a solution of 4.0 g (0.07 mole) of propargyl alcohol in 5 ml of absolute HEMPTA was added. The mixture was stirred for 1 hour at 40°C, a solution of 14.0 g (0.05 mole) of 1-iodoundecadiyne-(2,5) in 10 ml of absolute HEMPTA was added, and the temperature was kept at 60°–70°C for 5 hours, while stirring. After this time, the mixture was cooled, saturated $NH_4Cl$ solution was added, and the smeary residue which separated out was filtered off and extracted with ether in an extractor. After washing the ether extract with $NH_4Cl$ solution, water, $NH_4Cl$ solution and again with water, the extract was dried and filtered and the solvent was evaporated off in vacuo. 10.0 g of tetradecatriyn-(2,5,8)-ol-(1) remained; this material had an IR spectrum and an NMR spectrum which proved the assumed structure.

PREPARATION OF STARTING COMPOUNDS

Example A

4-Tetrahydropyranyloxy-1-iodobutyne-(2)

162.0 g (0.5 mole) of the tosylate of 4-tetrahydropyranyloxybutyn-(2)-ol-(1), melting point 44°–46°C, were dissolved in 500 ml of acetone and the solution was added dropwise to a solution of 187.5 g (1.25 moles) of sodium iodide in 500 ml of acetone at 40°C; sodium p-toluenesulphonate soon began to separate out. After warming and stirring at 40°–50°C for 2 hours, the mixture was cooled and the white salt mass was filtered off and rinsed with acetone, the acetone was stripped off in a rotary vacuum evaporator and the residue was taken up in ice water and ether. Washing and drying the ether phase gave 132.0 g (95% of theory) of 1-iodo-4-THP-butyne-(2) ($n_D^{20}$ = 1.5483) and the IR and NMR spectrum of which agreed completely with the structure. For analytical purposes, the 4-THP-1-iodobutyne-(2) could be applied to $Al_2O_3$ of activity II (acid), and eluted, with petroleum ether (low-boiling, 30°–50°C).

Example B

1-Iodooctyne-(2)

61.0 g (0.52 mole) of 1-hydroxyoctyne-(2) (prepared from 3-THP-propyne-(1) and 1-iodopentane, and saponification of the 1-THP-octyne-(2) so formed in a manner known from the literature) were dissolved in 150 ml of absolute ether and allowed to run into a solution of 100.0 g of tosyl chloride in 400 ml of absolute ether. After cooling to 0°C in a $N_2$ atmosphere, 32.0 g of powdered KOH were introduced in portions. When it had all been introduced, the mixture was warmed to room temperature and stirred for 2 hours. After pouring onto ice, the mixture was extracted with ether and the extract was washed with water and dried. After evaporating the solvent, 110 g of crude tosylate remained and were immediately converted into the iodide.

110 g of crude tosylate (0.393 mole) were dissolved in 200 ml of absolute acetone and added dropwise to a solution of 180 g (1.2 moles) of NaI in 600 ml of absolute acetone; a salt paste was produced, which was stirred for 3 hours at 40°–50°C. Working-up gave 76.5 g (80% of theory), which after chromatography on $Al_2O_3$ of activity II (acid), using petroleum ether, gave 75.5 of very pure 1-iodooctyne-(2) (boiling point 63°–65°C/0.1 mm Hg; $n_{20}^D$ 1.5332) with an NMR spectrum and an IR spectrum that were fully appropriate to the assumed structure.

Example C

1-Iodoundecadiyne-(2,5)

57.1 g (0.348 mole) of undecadiyn-(2,5)-ol-(1) were dissolved in 150 ml of absolute ether and allowed to run into a solution of 76.2 g (0.4 mole) of tosyl chloride in 600 ml of absolute ether. 28.0 g (0.5 mole) of powdered KOH were introduced in portions at 0°C under a $N_2$ atmosphere and after completion of the introduction the mixture was warmed to room temperature for 2 hours. It was poured onto ice and repeatedly extracted with ether; the ether phase was washed until neutral, dried over $Na_2SO_4$ and filtered, and the solvent was evaporated off in vacuo. 93.0 g of crude tosylate remained and were immediately reacted further to form the iodide.

115 g of NaI were dissolved in 500 ml of acetone and a solution of 93.0 g of the tosylate in 100 ml of acetone was added dropwise at 30°–40°C in a $N_2$ atmosphere. After stirring for 5 hours at 50°C, a salt precipitate formed, which was filtered off and washed with a little acetone. The acetone was largely removed on a rotary evaporator and the residue was treated with ice water and ether. 63.9 g of crude 1-iodoundecadiyne-(2,5) remained and were filtered over $Al_2O_3$ of activity II (acid) using petroleum ether. 61.0 g of 1-iodoundecadiyne-(2,5) remained; this could be distilled in a bulb tube at boiling point 100°–120°C/0.001 mm Hg (air bath temperature), without leaving any residue.

What is claimed is:

1. A process which comprises
   a. forming an intermediate complex by combining, in an organic solvent, at temperature of from −40° to +100°C and in the presence of at least one antioxidant,
      i. a molar equivalent amount of a copper(I) halide or copper(I) cyanide,
      ii. from 1 to 1.5 molar equivalent amount of an ethynyl reactant of the formula:
         $$R^1C \equiv CH$$
         in which $R^1$ is hydrogen, alkyl of 1 to 12 carbon atoms, alkenyl of 2 to 12 carbon atoms, alkynyl of 2 to 12 carbon atoms, polyalkenyl of up to 12 carbon atoms, polyalkynyl of up to 12 carbon atoms, or said alkyl, alkenyl, alkynyl, polyalkenyl or polyalkynyl substituted by tetrahydropyranyloxy, tri(lower alkyl)silyl, hydroxy, carboxy, carbo(lower alkoxy), carboxamide or a group of the formula:

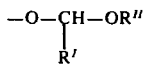

in which each of $R^I$ and $R^{II}$ is alkyl of 1 to 5 carbon atoms; and
      iii. from 1 to 1.5 molar equivalent amount of 1,8-diazabicyclo[5.4.0]undecene or 1,5-diazabicyclo[4.3.0]nonene, and
   b. combining with said complex at least a molar equivalent amount of a second reactant of the formula:
      $$XR^2$$
      in which X is chloro, bromo or iodo and $R^2$ is a mono- or poly-unsaturated aliphatic hydrocarbon of up to 12 carbon atoms, unsubstituted or substituted by tetrahydropyranyloxy, tri(lower alkyl)silyl, hydroxy, carboxy, carbo(lower alkoxy), carboxamide or a group of the formula:

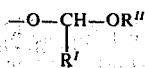

wherein each of $R^I$ and $R^{II}$ is alkyl of 1 to 5 carbon atoms; said $R^2$ being selected so that X is comprised in said $XR^2$ on a terminal 3-X-prop-1-en-1-yl or 3-X-prop-1-yn-1-yl group, thereby coupling the ethynyl group of ethynyl reactant with the prop-1-en-1-yl or prop-1-yn-1-yl group of said second reactant to form a compound of the formula:
   $$R^1C \equiv CR^2$$
   in which $R^1$ and $R^2$ are as defined above.

2. A process according to claim 1 wherein $R^1$ is alkyl of 1 to 12 carbon atoms, alkenyl of 2 to 12 carbon atoms, alkynyl of 2 to 12 carbon atoms, said alkyl, alkenyl or alkynyl being unsubstituted or substituted by tetrahydropyranyloxy, tri(alkyl)silyl of 1 or 2 carbon atoms, or hydroxy.

3. A process according to claim 1 wherein $R^1$ is alkyl of up to 5 carbon atoms, unsubstituted or substituted by hydroxy, tri(alkyl)silyl, or tetrahydropyranyloxy and
   $R^2X$ is of the formula:
   $$X-CH_2CH=CH-R''$$
   or
   $$X-CH_2C \equiv C-R''$$
   in which $R''$ is hydrogen, alkyl of up to 12 carbon atoms, alkenyl of up to 12 carbon atoms, or alkynyl of up to 12 carbon atoms, said alkyl, alkenyl and alkynyl being unsubstituted or substituted by hydroxy, tri(alkyl)silyl or tetrahydropyranyloxy, and X is bromo or chloro.

4. A process according to claim 1 wherein the copper(I) halide is copper(I) chloride, copper(I) bromide or copper(I) iodide.

5. A process according to claim 1 wherein the antioxidant is an hydroxylammonium salt, hydrazine, a hydrazinium salt, phenothiazine, ascorbic acid, a tertiary butylphenol or a mixture thereof.

6. A process according to claim 5 wherein the antioxidant is a hydroxylammonium salt.

7. A process according to claim 5 wherein the antioxidant is a mixture of an hydroxylammonium salt and phenothiazine.

8. A process according to claim 5 wherein the antioxidant is a mixture of phenothiazine and ascorbic acid.

9. A process according to claim 1 wherein the process is carried out at between −10° C and +60° C.

10. A process according to claim 1 wherein the organic solvent is acetonitrile, tetrahydrofuran, dimethylformamide, benzene, dioxane, dimethylsulphoxide, hexamethylphosphoric acid triamide or a mixture thereof.

11. A process according to claim 1 wherein the organic solvent is aqueous.

12. The process according to claim 1 for the production of 1-trimethylsilyl-6-tetrahydropyranyloxyhexadiyne-(1,4) wherein 3-tetrahydropyranyloxypropyne-(1) is reacted in a mixture comprising copper(I) chloride, 1,5-diazabicyclo[4,3,0]nonene and hydroxylammonium chloride with silylated propargyl bromide.

13. The process according to claim 1 for the production of 6-tetrahydropyranyloxy-hexen-(1)-yne-(4)

wherein 3-tetrahydropyranyloxypropyne-(1) is reacted in a mixture comprising copper(I) chloride, 1,8-diazabicyclo[5,4,0]undecene and hydroxylamine hydrochloride with allyl bromide.

14. The process according to claim 1 for the production of 1-tetrahydropyranyloxyundecadiyne-(2,5) wherein 1-bromo-4-tetrahydropyranyloxy-butyne-(2) is reacted in a mixture comprising copper(I) chloride, 1,5-diazabicyclo[4,3,0]nonene and hydroxylamine hydrochloride with heptyne-(1).

15. The process according to claim 1 for the production of 1,7-bis-tetrahydropyranyloxy-heptadiyne-(2,5) wherein tetrahydropyranyloxy-propyne-(1) is reacted in a mixture comprising copper(I) chloride, 1,5-diazabicyclo[4,3,0]nonene and hydroxylamine hydrochloride with 1-bromo-4-tetrahydropyranyloxy-butyne-(2).

16. The process according to claim 1 for the production of 1-tetrahydropyranyloxyundecadiyne-(2,5) wherein 1-bromo-4-tetrahydropyranyloxy-butyne-(2) is reacted in a mixture comprising copper(I) bromide, 1,8-diazabicyclo[5,4,0]-undecene and a mixture of phenothiazine and ascorbic acid with heptyne-(1).

17. The process according to claim 1 for the production of 1-tetrahydropyranyloxyundecadiyne-(2,5) wherein 4-tetrahydropyranyloxy-1-iodobutyne-(2) is reacted in a mixture comprising copper(I) iodide, 1,8-diazabicyclo[5,4,0]undecene and a mixture of hydroxylammonium sulphate and phenothiazine with heptyne-(1).

18. The process according to claim 1 for the production of undecadiyn-(2,5)-ol-(1) wherein propargyl alcohol is reacted in a mixture of copper(I) iodide, 1,8-diazabicyclo[5,4,0]undecene and a mixture of hydroxylammonium sulphate and phenothiazine with 1-iodooctyne-(2).

19. The process according to claim 1 for the production of hexen-(5)-yn-(2)-ol-(1) wherein propargyl alcohol is reacted in a mixture of copper(I) iodide, 1,8-diazabicyclo[5,4,0]undecene and a mixture of hydroxylammonium sulphate and phenothiazine with allyl bromide.

20. The process according to claim 1 for the production of tetradecatriyn-(2,5,8)-ol-(1) wherein propargyl alochol is reacted in a mixture of copper(I) iodide, 1,8-diazabicyclo[5,4,0]undecene and a mixture of hydroxylammonium sulphate and phenothiazine with 1-iodoundecadiyne-(2,5).

* * * * *